United States Patent [19]

Kropfgans et al.

[11] Patent Number: 5,654,459

[45] Date of Patent: Aug. 5, 1997

[54] PROCESS FOR PREPARING ALKYLHYDROGENCHLOROSILANES

[75] Inventors: Frank Kropfgans; Albert Frings; Michael Horn; Peter Jenkner; Hans-Joachim Koetzsch; Jaroslaw Monkiewicz; Claus-Dietrich Seiler, all of Rheinfelden; Hans-Guenther Srebny, Duelmen; Burkhard Standke, Loerrach, all of Germany

[73] Assignee: Huels Aktiengesellschaft, Marl, Germany

[21] Appl. No.: 659,819

[22] Filed: Jun. 7, 1996

[30] Foreign Application Priority Data

Jun. 7, 1995 [DE] Germany .................. 195 20 737.8

[51] Int. Cl.$^6$ .................................................. C07F 7/08
[52] U.S. Cl. ............................................................ 556/469
[58] Field of Search ............................................... 556/469

[56] References Cited

U.S. PATENT DOCUMENTS

| | | | |
|---|---|---|---|
| 3,769,310 | 10/1973 | Viego et al. | 556/469 |
| 4,567,286 | 1/1986 | Lepage et al. | 556/469 |
| 4,746,752 | 5/1988 | Lepage et al. | 556/469 |
| 4,973,725 | 11/1990 | Lewis et al. . | |
| 5,252,768 | 10/1993 | Geisberger et al. | 556/469 |

FOREIGN PATENT DOCUMENTS

| | | |
|---|---|---|
| 0 000 184 | 1/1979 | European Pat. Off. . |
| 0 652 221 | 5/1995 | European Pat. Off. . |
| 2 467 855 | 4/1981 | France . |
| 32 08 829 | 12/1982 | Germany . |
| 34 36 381 | 4/1986 | Germany . |
| 42 40 730 | 6/1994 | Germany . |

OTHER PUBLICATIONS

M.T. Bopohkob, 542.941.7, pp. 698–700, 1973.

*Primary Examiner*—Paul F. Shaver
*Attorney, Agent, or Firm*—Oblon, Spivak, McClelland, Maier & Neustadt, P.C.

[57] ABSTRACT

Alkylhydrogenchlorosilanes of formula I:

$$R_xHSiCl_y \qquad (I)$$

wherein R are identical or different alkyl radicals, x is 1 or 2 and y is 1 or 2 and the sum of x and y is equal to 3, are prepared by comproportionating alkylchlorosilanes of formula II:

$$R_aSiCl_n \qquad (II)$$

wherein R denotes identical or different alkyl radicals, a is 1 or 2 and n is 2 or 3 and the sum of a and n is equal to 4 with hydrogenchlorosilanes of formula III:

$$R_bH_cSiCl_{4-b-c} \qquad (III)$$

wherein R denotes identical or different alkyl radicals, b is 0, 1, 2 or 3 and c is 1, 2, 3 or 4 and the sum of b and c is equal to or smaller than 4, in the presence of a catalyst saturated with a hydrogen halide.

19 Claims, No Drawings

PROCESS FOR PREPARING ALKYLHYDROGENCHLOROSILANES

BACKGROUND OF THE INVENTION

1. Field of the Invention

The present invention relates to a process for preparing alkylhydrogenchlorosilanes.

2. Description of the Background

Alkylhydrogenchlorosilanes are important, inter alia, as stereoregulating catalyst components which are useful for example, in the polymerization of olefins. In addition, such alkylhydrogenchlorosilanes serve to introduce reactive groups into silicones and are used for the preparation of organofunctional silanes and protecting group reagents.

It is known that of the type of compounds of the formula I infra, only methylhydrogendichlorosilane is available on a large scale as a byproduct from the Müller-Rochow synthesis, but this alone is not sufficient to meet the specific requirements for progress in fields of application described supra. The urgently needed dimethylhydrogenchlorosilane, which likewise occurs in very low concentrations in the crude product from the Müller-Rochow synthesis, can be isolated only partially from a reaction product and with considerable technical effort. Moreover, the product is obtained in only unsatisfactory purity, so that it is essentially unavailable for possible large-scale applications. Many attempts have therefore already been made to find other synthetic routes to the compound.

One proposal for the synthesis of dimethylhydrogenchlorosilane is a Müller-Rochow synthesis which is conducted in the presence of hydrogen (e.g., U.S. Pat. No. 4,973,725). Although very high proportions of methylhydrogenchlorosilanes are formed in this way, methylhydrogendichlorosilane predominates here too. Thus this synthetic route is not economical for the preparation of dimethylhydrogenchlorosilane and also does not represent a synthetic route independent of coupled production of other products.

Attempts have also been made to obtain dimethyldichlorosilane by catalytic comproportionation which, however, leads to only very small conversions with large material losses, even under drastic conditions. Voronkov reacted dimethyldichlorosilane with dihydrogenorganochlorosilanes in the presence of a high concentration of Friedel-Crafts catalyst, by removing the resulting dimethylchlorosilane from the reaction equilibrium by distillation (M. G. Voronkov, L. A. Abramas, *Jzv. Akad. Nauk SSSR, Ser. Khim.* 1974 (3), 698–700) In this reaction, dihydrogenorganochlorosilane supplies hydrogen. However, the Voronkov process is too complicated for large-scale use. In particular, the formation of relatively large amounts of residues, which are difficult to dispose of, is an obstacle to industrial realization.

The above difficulties are also particularly true for attempts to prepare such doubly alkylated hydrogenchlorosilanes by means of the Grignard reaction.

It has also been proposed to conduct the Voronkov hydrogenation in the presence of ammonium halide catalysts immobilized on silica gel (DE-A 42 40 730). Ammonium halides immobilized on silica gels do not have sufficient stability at temperatures above 120° C. and have a catalyst service life which is too short for continuous operation under the reaction conditions to be employed. A need therefore continuous to exist for an improved process of preparing dimethyl hydrogenchlorosilane in greater yield and purity.

SUMMARY OF THE INVENTION

Accordingly, one object of the present invention is to provide a process which makes it possible to prepare alkylhydrogenchlorosilanes of formula I infra in a simple and economical manner.

Briefly, these objects and other objects of the present invention as hereinafter will become more readily apparent can be obtained by a process for preparing alkylhydrogenchlorosilanes of formula I:

$$R_xHSiCl_y \quad (I)$$

wherein R denotes identical or different alkyl radicals, x is 1 or 2 and y is 1 or 2 and the sum of x and y is equal to 3, by comproportionation of alkylchlorosilanes of formula II:

$$R_aSiCl_n \quad (II)$$

wherein R denotes identical or different alkyl radicals, a is 1 or 2 and n is 2 or 3 and the sum of a and n is equal to 4, with hydrogenchlorosilanes of formula III:

$$R_bH_cSiCl_{4-b-c} \quad (III)$$

wherein R denotes identical or different alkyl radicals, b is 0, 1, 2 or 3 and c is 1, 2, 3 or 4 and the sum of b and c is equal to or smaller than 4.

It has now surprisingly been found that a compound of formula II above can be reacted in a simple and economical manner in admixture with a hydrogen-donating agent of formula III in the presence of a catalyst which has advantageously been previously saturated with hydrogen halide, giving the alkylhydrogenchlorosilane of formula I in good yield. For this purpose, the reaction mixture is generally passed with heating over a prepared catalyst bed. The crude product is isolated and purified subsequently using known distillation methods.

In formulae I, II and III identical or different alkyl substituents are represented by R. These substituents can be alkyl radicals having from 1 to 18 carbon atoms and have a linear, branched or cyclic structure. The alkyl radicals can be either saturated or unsaturated.

In the reaction of the process of the invention, a zirconium-containing and/or aluminum-containing catalyst is preferably used. The supports for these catalysts are advantageously porous and can have a total pore volume of, for example, from 0.01 to 10 cm³/g. Suitable catalysts are normally those whose catalyst support has a BET surface area of from 5 to 500 m²/g.

In the process of the invention, a preferred catalyst is based on zirconium oxide and/or aluminum oxide, with the oxide structures of the catalysts also possibly containing hydroxyl groups. The groups are particularly present on the catalyst surface, as are known for amphoteric to strongly acid inorganic oxide systems.

The zirconium and/or aluminum oxides or their oxide/hydroxides are generally not restricted to one modification. However, among the catalysts, not only γ-aluminum oxide, but also α-aluminum oxide and γ-aluminum oxide hydroxide are preferred. The catalyst support can be made in the form of extrudates, tubes, toothed wheels, spheres, chippings or powder.

The process of the invention can be carried out in a stirred tank reactor, a multitube reactor or in a fixed-bed reactor with or without recirculation, continuously or batchwise.

The reactor used is preferably a heatable tube provided with means to regulate the temperature, which contains a fixed bed catalyst and to which is fed the starting materials. The reacting materials, as is generally customary, are fed via metering devices and the reactor is provided with a mixing nozzle, a vaporizer and a preheater. The crude product arriving at the reactor outlet can either be passed directly to a continuous distillation process or, if desired, be liquified by cooling or quenching and then processed by distillation.

The process of the invention is preferably carried out at a temperature ranging from 60° C. to 290° C., and preferably under atmospheric pressure or elevated pressure, for example, up to 20 bar abs. These factors are selected as a function of the physical and reactive properties of the starting materials, and also the mean residence time τ which generally ranges from 1 minute to 20 minutes. That is, in the process of the invention, the reaction over the catalyst is preferably conducted over a period of from 1 to 20 minutes. The reaction is preferably conducted under atmospheric pressure. If desired, it is also possible to employ subatmospheric pressures. Advantages for the reactivity of some systems are gained and improved space-time yields are achieved by conducting the synthesis under subatmospheric pressure. Also, if desired, the reaction can be conducted in the liquid phase, under which condition the reaction is preferably carried out under atmospheric pressure or elevated pressure.

Preferred catalyst activity for the present reaction is generally achieved by treatment of the catalyst support with a hydrogen halide until saturation is reached, preferably by treatment with hydrogen chloride or hydrogen bromide. The saturated state is generally reached when the hydrogen halide is no longer absorbed, for example in a treatment of the catalyst support in a flow reactor, where towards the end of the treatment, hydrogen chloride again leaves the end of the reactor. The treatment temperature is generally not critical and can be above room temperature, for example at reaction temperature. Preferably, a catalyst saturated with hydrogen halide at temperatures ranging from 180° to 200° C. is used for the reaction.

The molar ratios of the starting materials of formulae II and III for the reaction can be equimolar. However, one starting material can be used for the reaction in a 10-fold to 12-fold excess or deficiency compared to the other reactant.

In order to prepare the desired target product in particularly good purity, the crude product prepared by the reaction of the present invention is worked up by distillation. Thus, an advantage of the present process is that it can be conducted continuously.

Examples of products of formula I which can be prepared by the process of the invention are as follows:
ethylhydrogendichlorosilane,
n-propylhydrogendichlorosilane,
isobutylhydrogendichlorosilane,
n-pentylhydrogendichlorosilane,
cyclopentylhydrogendichlorosilane,
cyclohexylhydrogendichlorosilane,
octylhydrogendichlorosilane,
decylhydrogendichlorosilane,
hexadecylhydrogendichlorosilane,
octadecylhydrogendichlorosilane,
dimethylhydrogenchlorosilane,
ethylmethylhydrogenchlorosilane,
diethylhydrogenchlorosilane,
propylmethylhydrogenchlorosilane,
dipropylhydrogenchlorosilane,
diisobutylhydrogenchlorosilane,
dicyclopentylhydrogenchlorosilane,
dicyclohexylhydrogenchlorosilane,
cyclohexylmethylhydrogenchlorosilane,
octadecylmethylhydrogenchlorosilane, and the like.

Suitable examples of alkylchlorosilanes of formula II include methyltrichlorosilane, dimethyldichlorosilane, trimethylchlorosilane, ethyltrichlorosilane, ethylmethyldichlorosilane, ethyldimethylchlorosilane, tert-butyldimethylchlorosilane, diethyldichlorosilane, propyltrichlorosilane, propylmethyldichlorosilane, dipropyldichlorosilane, isobutyltrichlorosilane, isobutylmethyldichlorosilane, diisobutyldichlorosilane, pentyltrichlorosilane, cyclopentyltrichlorosilane, cyclopentylmethyldichlorosilane, dicyclopentyldichlorosilane, cyclohexyltrichlorosilane, cyclohexylmethyldichlorosilane, dicyclohexyldichlorosilane, octyltrichlorosilane, decyltrichlorosilane, hexadecyltrichlorosilane, octadecylmethyldichlorosilane, and the like.

Suitable examples of hydrogensilanes of formula III include trichlorosilane, dichlorosilane, monochlorosilane, monosilane, methyldihydrogenchlorosilane, methyltrihydrogensilane, dimethyldihydrogensilane, ethyltrihydrogensilane, ethylmethyldihydrogensilane, diethyldihydrogensilane, propyltrihydrogensilane, propylmethyldihydrogensilane, dipropyldihydrogensilane, isobutyltrihydrogensilane, isobutylmethyldihydrogensilane, diisobutyldihydrogensilane, cyclopentyltrihydrogensilane, cyclopentylmethyldihydrogensilane, dicyclopentyldihydrogensilane, cyclohexyltrihydrogensilane, cyclohexylmethyldihydrogensilane, dioctyldihydrogensilane, octadecylmethyldihydrogensilane, 2-cyclohexenylethyltrihydrogensilane, and the like.

Having generally described this invention, a further understanding can be obtained by reference to certain specific examples which are provided herein for purposes of illustration only and are not intended to be limiting unless otherwise specified.

EXAMPLE 1

An upright reactor (about 2 liters capacity) comprised of a double-walled glass tube heated by means of a thermostat and having an internal diameter of 50 mm and a height of about 1000 mm was prepared. The reactor was charged with a catalyst comprised of granulated γ-Al$_2$O$_3$ having a particle size of from 1 to 3 mm which had been saturated at 180° C. with gaseous HCl. The homogeneous mixture of the starting materials was conveyed continuously via a vaporizer and a preheater into the reactor in a descending direction at the residence times shown in Table 1. The corresponding metering rates and operating temperatures are also provided in the table. After the reaction, the product mixture was condensed in a condenser and a downstream low-temperature condenser and finally isolated by the customary methods of column distillation.

Table 1 shows the results of conducting the process of the invention for preparing dimethylhydrogenchlorosilane from dimethyldichlorosilane and dimethylsilane under various conditions.

TABLE 1

| Dimethylhydrogenchlorosilane from dimethylsilane and dimethylchlorosilane | | | | |
|---|---|---|---|---|
| Reaction | Mixing ratio | | | Yield of |
| temperature [°C.] | (CH$_3$)$_2$SiH$_2$ [mol] | (CH$_3$)$_2$SiCl$_2$ [mol] | Residence time [min] | (CH$_3$)$_2$HSiCl [%] |
| 160 | 1 | 1 | 2.8 | 84 |
| | | | 5.3 | 96 |
| | | | 8.0 | ≈100 |

TABLE 1-continued

Dimethylhydrogenchlorosilane from dimethylsilane and dimethylchlorosilane

| Reaction temperature [°C.] | Mixing ratio | | | Yield of |
|---|---|---|---|---|
| | $(CH_3)_2SiH_2$ [mol] | $(CH_3)_2SiCl_2$ [mol] | Residence time [min] | $(CH_3)_2HSiCl$ [%] |
| 80 | 1 | 1 | 8.0 | 98 |
| | | | 5.3 | 92 |
| 80 | 0.7 | 1 | 10.5 | ≈100 |

EXAMPLE 2

Preparation of dimethylhydrogenchlorosilane from dimethyldichlorosilane and cyclohexyldihydrogenchlorosilane.

Using a method similar to Example 1, from a mixture of 520 g (4 mol) of dimethyldichlorosilane and 300 g (2 mol) of cyclohexyldihydrogenchlorosilane there were isolated, at a conversion of about 72% of the amount of dimethyldichlorosilane in about 9 hours at 224° C., a residence time of about 12 minutes and parallel distillation of the crude product with recycling of cyclohexylhydrogendichlorosilane and dimethyldichlorosilane, a total of 346 g (91%) of dimethylhydrogenchlorosilane and 412 g (95%) of cyclohexyltrichlorosilane.

EXAMPLE 3

Preparation of dimethylhydrogenchlorosilane from dimethyldichlorosilane and methyldihydrogenchlorosilane.

Using a method similar to Example 1, a mixture of 1045 g (8.1 mol) of dimethyldichlorosilane and 457 g (5.67 mol) of methyldihydrogenchlorosilane gave, in about 36 operating hours at 237° C. and a residence time of about 14 minutes, a crude product having the following composition according to gas chromatography:

| | |
|---|---|
| methyldihydrogenchlorosilane | 1.9% |
| methylhydrogendichlorosilane | 27.1% |
| dimethylhydrogenchlorosilane | 45.7% |
| methyltrichlorosilane | 18.0% |
| dimethyldichlorosilane | 7.3% |

Careful distillation of the product by a laboratory column having 40 theoretical plates gave 679 g of dimethylhydrogenchlorosilane (89% yield, based on dimethyldichlorosilane and on the theoretically possible transfer of silane-hydrogen bonds, or 67% of the total SiH used).

EXAMPLE 4

Using a method similar to Example 1, a catalyst charge comprising granulated $ZrO_2$, having a particle size of about 2 mm, was saturated with HBr at 180° C. A mixture of methylhydrogendichlorosilane and dimethyldichlorosilane in a molar ratio of 2.5:1 was reacted over this catalyst at a reaction temperature of 142° C. and a residence time of 16 minutes. The resulting crude product had the following composition according to gas chromatography:

| | |
|---|---|
| methyldihydrogenchlorosilane | 0.4% |
| methylhydrogendichlorosilane | 48.9% |
| dimethylhydrogenchlorosilane | 16.8% |
| methyltrichlorosilane | 25.9% |
| dimethyldichlorosilane | 8.0% |

In 28 operating hours, 346 g (2.68 mol) of dimethyldichlorosilane and 770 g (6.7 mol) of methylhydrogendichlorosilane gave about 1100 g of crude product from which 182 g of dimethylhydrogenchlorosilane were isolated by distillation. This corresponds to a conversion of 72% for the dimethyldichlorosilane.

EXAMPLE 5

Preparation of cyclopentylhydrogendichlorosilane from cyclopentyltrichlorosilane and cyclopentyldihydrogenchlorosilane.

Using a method similar to Example 1, a mixture of 204 g of cyclopentyltrichlorosilane and 135 g of cyclopentyldihydrogenchlorosilane, b.p. 138° C., (molar ratio 1:1) gave, at 187° C. and an average residence time of 6 minutes and an operating time of about 2 hours, 166 g (98% yield) of cyclopentylhydrogendichlorosilane, b.p. 54° C. (9 torr).

EXAMPLE 6

Preparation of dimethylhydrogenchlorosilane from dimethyldichlorosilane and methylsilane.

Using a method similar to Example 1, a mixture of methylsilane and dimethyldichlorosilane in a molar ratio of about 0.35:1 gave, at 195° C. and residence times between 15 and 20 minutes, the target product in a yield of about 97%. The main by-product was methyltrichlorosilane.

EXAMPLE 7

Preparation of isobutylhydrogendichlorosilane from isobutyltrichlorosilane and isobutylsilane.

Using a method similar to Example 1, 383 g of isobutyltrichlorosilane and 177 g of isobutyltrihydrogensilane gave, in about 3 hours of operation at 180° C. and a residence time of about 4 minutes, about 600 g (about 95% yield) of isobutylhydrogendichlorosilane, b.p. 122° C.

EXAMPLE 8

Preparation of isobutylmethylhydrogenchlorosilane from isobutylmethyldichlorosilane and isobutylmethylsilane.

Using a method similar to Example 1, isobutylmethyldichlorosilane and isobutylmethylsilane in a molar ratio of 1:1 were reacted at 168° C. and a residence time of about 10 minutes to give isobutylmethylhydrogenchlorosilane, b.p. 121°–123° C., with a product yield of 94%. In an operating time of 4 hours, 171 g of isobutylmethyldichlorosilane and 102 g of isobutylmethylsilane were used and 154 g of target product were isolated therefrom.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for preparing alkylhydrogenchlorosilanes of formula I:

$$R_xHSiCl_y \qquad (I)$$

wherein R denotes identical or different alkyl radicals, x is 1 or 2 and y is 1 or 2 and the sum of x and y is equal to 3, comprising:

comproportionating alkylchlorosilanes of formula II:

wherein R denotes identical or different alkyl radicals, a is 1 or 2 and n is 2 or 3 and the sum of a and n is equal to 4, with hydrogenchlorosilanes of formula III:

wherein R denotes identical or different alkyl radicals, b is 0, 1, 2 or 3 and c is 1, 2, 3 or 4 and the sum of b and c is equal to or smaller than 4, in the presence of a catalyst saturated with a hydrogen halide.

2. The process as claimed in claim 1, wherein the catalyst for the reaction contains zirconium and/or aluminum.

3. The process as claimed in claim 1, wherein the catalyst for the reaction is based on zirconium and/or aluminum oxide.

4. The process as claimed in claim 1, wherein the catalyst for the reaction is saturated with hydrogen chloride or hydrogen bromide.

5. The process as claimed in claim 1, wherein the catalyst for the reaction is saturated with hydrogen halide above room temperature.

6. The process as claimed in claim 5, wherein the catalyst for the reaction is saturated with hydrogen halide in the temperature ranging from 180° to 200° C.

7. The process as claimed in claim 1, wherein the reaction is conducted at a temperature ranging from 60° to 290° C.

8. The process as claimed in claim 1, wherein the reaction is conducted under atmospheric pressure or elevated pressure.

9. The process as claimed in claim 1, wherein the reaction over the catalyst is conducted over a period of from 1 to 20 minutes.

10. The process as claimed in claim 1, wherein the crude product is further purified by distillation.

11. The process as claimed in claim 1, wherein the process is conducted continuously.

12. The process as claimed in claim 1, wherein the catalyst is supported on a support having a surface area of 5 to 500 m²/g.

13. The process as claimed in claim 1, wherein the catalyst is supported on a support having a total pore volume of 0.01 to 10 cm³/g.

14. The process as claimed in claim 1, wherein the alkylchlorosilane of formula II is selected from the group consisting of methyltrichlorosilane, dimethyldichlorosilane, trimethylchlorosilane, ethyltrichlorosilane, ethylmethyldichlorosilane, ethyldimethylchlorosilane, tert-butyldimethylchlorosilane, diethyldichlorosilane, propyltrichlorosilane, propylmethyldichlorosilane, dipropyldichlorosilane, isobutyltrichlorosilane, isobutylmethyldichlorosilane, diisobutyldichlorosilane, pentyltrichlorosilane, cyclopentyltrichlorosilane, cyclopentylmethyldichlorosilane, dicyclopentyldichlorosilane, cyclohexyltrichlorosilane, cyclohexylmethyldichlorosilane, dicyclohexyldichlorosilane, octyltrichlorosilane, decyltrichlorosilane, hexadecyltrichlorosilane, and octadecylmethyldichlorosilane.

15. The process as claimed in claim 1, wherein the hydrogensilane of formula III is selected from the group consisting of trichlorosilane, dichlorosilane, monochlorosilane, monosilane, methyldihydrogenchlorosilane, methyltrihydrogensilane, dimethyldihydrogensilane, ethyltrihydrogensilane, ethylmethyldihydrogensilane, diethyldihydrogensilane, propyltrihydrogensilane, propylmethyldihydrogensilane, dipropyldihydrogensilane, isobutyltrihydrogensilane, isobutylmethyldihydrogensilane, diisobutyldihydrogensilane, cyclopentyltrihydrogensilane, cyclopentylmethyldihydrogensilane, dicyclopentyldihydrogensilane, cyclohexyltrihydrogensilane, cyclohexylmethyldihydrogensilane, dioctyldihydrogensilane, octadecylmethyldihydrogensilane, and 2-cyclohexenylethyltrihydrogensilane.

16. The process as claimed in claim 1, wherein the molar ratio of reacting silanes of formulas II and III ranges up to a 12-fold excess of one silane to the other.

17. The process as claimed in claim 16, wherein said excess ranges up to a ten-fold excess.

18. The process as claimed in claim 16, wherein said molar ratio of reactants is 1:1.

19. The process as claimed in claim 12, wherein said support is in the shape of extrudates, tubes, toothed wheels, spheres, chippings or powder.

* * * * *